(12) United States Patent
Clinton

(10) Patent No.: US 6,541,214 B1
(45) Date of Patent: Apr. 1, 2003

(54) N-TERMINALLY TRUNCATED HER-2/NEU PROTEIN AS A CANCER PROGNOSTIC INDICATOR

(75) Inventor: Gail M. Clinton, Portland, OR (US)

(73) Assignee: Oregon Heath Science University, Portland, OR (US)

( * ) Notice: Subject to any disclaimer, the term of this patent is extended or adjusted under 35 U.S.C. 154(b) by 0 days.

(21) Appl. No.: 09/192,206

(22) Filed: Nov. 13, 1998

(51) Int. Cl.[7] ............... G01N 33/574; G01N 33/567; G01N 33/543; A61K 38/00; C07K 2/00

(52) U.S. Cl. ............... 435/7.23; 435/7.1; 435/7.2; 435/7.21; 435/7.92; 530/300; 530/350; 530/386; 530/387.1; 530/388.1; 530/388.15; 530/388.2; 530/389.1; 530/389.7; 530/388.8

(58) Field of Search ............... 435/4, 7.1, 7.2, 435/7.21, 7.23, 7.92; 530/350, 386, 387.1, 300, 388.1, 388.15, 388.2, 389.1, 389.7, 388.8, 308

(56) References Cited

U.S. PATENT DOCUMENTS 5,677,171 A    10/1997  Hudziak et al.
5,811,098 A  * 9/1998   Plowman et al.
5,876,712 A  * 3/1999   Cheever et al.

OTHER PUBLICATIONS

Myers et al. Elevated serum levels of p105(erbB–2) in patients with advanced–stage prostatic adenocarcinoma. Int. J. Cancer (Pred. Oncol.) 69:398–402, 1996.*

Meden et al. Elevated serum levels of a c–erbB–2 oncogene produc in ovarian cancer patients and in pregnancy. J. Cancer Res. Clin. Oncol. 120:378–381, 1994.*

Christianson, Tracy A. et al., $NH_2$–terminally Truncated HER–2/neu Protein: Relationship with Shedding of the Extracellular Domain and with Prognostic Factors in Breast Cancer, *Cancer Research* 58:5123–5129, Nov. 15, 1998.

Zebrecky et al., The extracellular domain of p185/neu is released from the surface of human breast carcinoma cells, SK–BR–3. *Journal of Biological Chemistry*, Jan. 25, 1991, vol. 266, No. 3, pp. 1716–1720.

Press et al. Her–2/neu expression in node–negative breast cancer: direct tissue quantitation by computerized image analysis and association of overexpression with increased risk of recurrent disease. *Cancer Research*, Oct. 15, 1993, vol. 53, pp. 4960–4970.

Valerón et al. Quantitative analysis of $p185^{HER-2/neu}$ protein in breast cancer and its association with other prognostic factors. *Int. J. Cancer* (Pred. Oncol.) 1997, vol. 74, pp. 175–179.

Christianson, Tracy A. et al., $NH_2$–terminally Truncated HER–2/neu Protein: Relationship with Shedding of the Extracellular Domain and with Prognostic Factors in Breast Cancer, *Cancer Research* 58:5123–5129, Nov. 15, 1998.

* cited by examiner

*Primary Examiner*—Yvonne Eyler
*Assistant Examiner*—Alana M. Harris
(74) *Attorney, Agent, or Firm*—Barry L. Davison; Davis Wright Tremaine

(57) ABSTRACT

There is disclosed an initial identification of an N-terminally truncated HER-2/neu product. This product is a 95 kDa polypeptide having in vitro kinase activity (as determined by western blotting). Moreover, immunoprecipitations using domain specific antibodies was able to utilize this specific polypeptide from intracellular fragments as a diagnostic and prognostic indicator of adenomacarcinomas without the severe dilution effects encountered by measuring ECD.

16 Claims, 6 Drawing Sheets

N-TERMINALLY TRUNCATED HER-2/NEU PROTEIN AS A CANCER PROGNOSTIC INDICATOR

TECHNICAL FIELD OF THE INVENTION

The present invention provides an N-terminally truncated HER-2/neu polypeptide, p95HER-2, that is useful as a diagnostic and prognostic indicator for breast cancer. The present invention further provides a 12–15 amino acid "extracellular stub" polypeptide that is also a useful epitope for an immunological assay for diagnosis and prognosis of various adenocarcinomas, particularly breast cancer and ovarian cancer.

The present invention was made with funding from the United States Government under grant CA-71447 from the National Cancer Institute and DAMD17-6204 from the Department of Defense (DOD) Breast Cancer Research Program. The United States Government may have certain rights in this invention.

BACKGROUND OF THE INVENTION

The HER-2/neu (erbB-2) gene encodes a receptor-like tyrosine kinase (RTK) which is a member of the epidermal growth factor receptor family (Coussens et al., *Science* 230:1132–1139, 1985). Overexpression of HER-2/neu has been observed in tumors arising at many sites including non-small cell lung (Kern et al., *Cancer Res.* 50:5184–5191, 1990), colon (Cohen et al., *Oncogene*, 4:81–88, 1989), prostate (Arai et al., *Prostate* 30:195–201, 1997), ovarian, and breast (Slamon et al., *Science* 244: 707–712, 1989). In human breast cancer, where HER-2/neu involvement has been studied, overexpression occurs in 15–30% of the cases (Singleton and Strickler, *Pathol.Annual* 27 Pt 1:165–198, 1992) and predicts for significantly lower survival rate and shorter time to relapse in patients with lymph node positive disease (Slamon et al., *Science* 244: 707–712, 1989; Singleton and Strickler, *Pathol.Annual* 27 Pt 1:165–198, 1992; Slamon et al., *Science* 235:177–182, 1987; and Slamon et al., *Science* 235:177–182, 1987). The significance of HER-2/neu in node negative patients is controversial and so far its clinical utility as a prognostic indicator is limited (Slamon et al., *Science* 235:177–182, 1987; and Hynes et al., *Biochem. Biophys. Acta* 1198:165–184, 1994). Various approaches are being taken toward HER-2/neu targeted therapeutics many of which are based on antibodies specific to the extracellular domain (ECD) of the transmembrane protein, which either down regulate receptor function or target recombinant toxins with the goal of specifically killing HER-2/neu expressing tumor cells (Hynes et al., *Biochem. Biophys. Acta* 1198:165–184, 1994; Press et al., *Progress in Clinical & Biological Research* 354: 209–221, 1990; and Dougall et al., *Oncogene* 9: 2109–2123, 1994).

In addition to the full length transmembrane product, p185, of the HER-2/neu gene, a truncated product corresponding to the extracellular domain (ECD) is released from breast carcinoma cells in culture by regulated proteolysis (Lin and Clinton, *Oncogene* 6:639–643, 1991; Zabrecky et al., *J. Biol. Chem.* 266: 1716–1720, 1991; and Pupa et al., *Oncogene*, 8:2917–2923, 1993), and is also produced from an alternative transcript (Scott et al., *Mol. Cell. Biol.*, 13:2247–2257 1993). HER-2/neu ECD is elevated in the serum of patients with breast (Leitzel et al., *J. Clin. Oncol.* 10:1436–1443, 1992), ovarian (Maden et al., *Anticancer Res.* 17:757–760, 1997), and prostate cancer (Myers et al., *Int. J. Cancer* 69 398–402, 1996). Several studies of breast cancers estimate that 6% or less of early stage breast cancer, about 25% of patients with metastatic and locally advanced disease, and greater than 50% of patients with recurrent metastatic disease have elevated serum ECD (Brandt-Rauf et al., *Mutation Res.* 333:203–208, 1995). Elevated ECD, in serum is associated with overexpression of HER-2/neu in tumor tissue and also has been correlated to tumor load (Molina et al., *Br. J. of Cancer* 4:1126–1131, 1996; and Brodowicz et al., *Oncology* 54:475–481, 1997). Serum ECD is a marker of metastatic disease and may predict recurrence (Molina et al., *Br. J. of Cancer* 4:1126–1131, 1996), shortened survival (Brodowicz et al., *Oncology* 54:475–481, 1997; Kandl et al., *Br. J. Cancer* 70:739–742, 1994; Fehm et al., *Oncology* 55:33–38, 1998 and Mansour et al., *Anticancer Res.* 17:3101–3105, 1997), and response to antiestrogen therapy in advanced stage patients (Leitzel et al., *J. Clin. Oncol.* 13:1129–1135, 1995; and Yamauchi et al., *J. Clin. Oncol.* 15:2518–2525, 1997). Serum ECD has also been reported to neutralize the activity of anti HER-2/neu antibodies targeted to the ECD (Baselga et al., *J. Clin. Oncol.* 14:737–744, 1996; and Brodowicz et al., *Int. J. Cancer.* 73:875–879, 1997) possibly allowing escape of HER-2-rich tumors from immunological control.

Cellular fragments created by ectodomain shedding have been described for the colony stimulating factor receptor (CSF-1R) (Downing et al., *Mol. Cell. Biol.* 9:2890–2896, 1989), the TrkA neurotrophin receptor (Cabrera et al., *J. Cell. Biol.* 132 427–436, 1996), Axl receptor (O'Bryan et al., *J. Biol. Chem.*, 270.551–557, 1995), and HER-4 (Vecchi et al., *J. Biol. Chem.* 271:18989–18995, 1996). However, a truncated cellular product of HER-2/neu shedding has not been identified. The truncated CSF-1R was found to have in vitro kinase activity (Downing et al., *Mol. Cell. Biol.* 9:2890–2896, 1989), and the cytoplasmic HER-4, induced by phorbol ester tumor promoters, had little or no kinase activity (Vecchi et al., *J. Biol. Chem.* 271:18989–18995, 1996) while a truncated HER-4 found in cells treated with a proteosome inhibitors was an active kinase (Vecchi et al., *J. Cell. Biol.* 139:995–1003, 1997). Therefore, there is a need in the art to identify a truncated HER-2/neu polypeptide and determine if it has enzymatic activity in general or kinase activity in particular. Moreover, such a truncated polypeptide is likely to be a better marker for tumor diagnosis, screening and prognosis as it will be easier to assay for the polypeptide than to assay for shed ECD, which is present in a much more dilute form.

The ECD of full-length transmembrane receptors often exerts a negative regulatory constraint on their signaling activity. Engineered deletion of a region of the HER-2 ECD was found to enhance its oncogenic potency (DiFiore et al., *Science* 237:178–182, 1987; Hudziak et al., *Proc. Natl. Acad. Sci. USA* 84: 7159–7163, 1987; Segatto et al., *Mol. Cell. Biol.* 8:5570–5574, 1988; and Bargmann and Weinberg, *EMBO J.* 7:2043–2052, 1988). This has also been illustrated by engineered removal of the ECD from the epidermal growth factor (EGF) receptor and by the oncogenic potency of viral encoded v-erbB, v-kit, and v-ros, that are missing regions of the ECD found in their normal cellular counterparts (Rodrigues and Park, *Curr. Opin. Genet. Dev.* 4:15–24, 1994). Naturally occurring mutant EGF receptors with N-terminal truncations have been identified in several human carcinomas (Moscatello et al., *Cancer Res.*, 55:5536–5539, 1995) and have constitutive signaling activity and enhanced oncogenic transforming activity in cell culture and animal models (Moscatello et al., *Oncogene* 13:85–96, 1996; and Huang, et al. *J. Biol. Chem.* 272:2927–2935, 1997).

Therefore, there is a need in the art to better study the HER-2/neu receptor and to determine if there are better regions of this protein available for using as a more sensitive diagnostic and prognostic indicator for breast cancer. Moreover, there is no procedure available to monitor for staging and prognosis of various adenocarcinomas, such as breast cancers, other than physically investigating adjacent tissue, such as regional lymph nodes and then sectioning the tissue by difficult histological techniques. Therefore, there is a need in the art to provide improved means for determining adenocarcinoma staging and further determining prognostic factors to guide appropriate treatment strategies. The present invention was made to address the foregoing needs in the art.

SUMMARY OF THE INVENTION

The present invention is based upon the initial identification of an N-terminally truncated HER-2/neu product. This product is approximately a 95 kDa polypeptide having in vitro kinase activity. Moreover, immunoprecipitation using domain specific antibodies was able to isolate this specific polypeptide from intracellular fragments for use as a diagnostic and prognostic indicator of various carcinomas without the severe dilution effects encountered by measuring ECD in blood/serum. The carcinomas for which the 95 kDa polypeptide will have diagnostic and prognostic value include, for example, carcinomas that overexpress HER-2, including breast, gastric, cervical, non-small cell lung, and prostate carcinomas.

The present invention provides a method for diagnostic and prognostic screening of a metastatic stage carcinoma that overexpresses HER-2, comprising:

(a) providing a suspected tissue sample having cells;

(b) lysing the cells to expose intracellular contents and form a lysate; and (c) measuring the lysate for the presence of 95HER-2 polypeptide.

Preferably, the lysing step is followed by an additional step separating soluble from insoluble material of the lysate to remove dense fibrous material. Preferably, the measuring step utilizes an assay procedure selected from the group consisting of Western blotting, immunochemistry, ELISA, and combinations thereof. Preferably, the carcinoma that overexpresses HER-2 is selected from the group consisting of breast cancer, gastric carcinoma, prostate cancer, non-small cell lung carcinoma, and ovarian carcinoma.

The present invention provides a method for diagnostic and prognostic screening of a metastatic stage carcinoma that overexpresses HER-2, comprising:

(a) providing a suspected tissue sample having cells;

(b) providing an antibody that binds to a stub region of HER-2, wherein the stub region is a polypeptide sequence of SEQ ID NO. 1 or a fragment thereof; and (c) determining the percentage of cells that have an exposed extracellular stub region.

Preferably, the means for determining the percentage of cells having an exposed extracellular stub region utilizes an assay procedure, wherein the assay procedure is selected from the group consisting of Western blotting, immunochemistry, red cell agglutination, ELISA, affinity chromatography, and combinations thereof. Preferably, the carcinoma that overexpresses HER-2 is selected from the group consisting of breast carcinoma, gastric carcinoma, prostate cancer, non-small lung carcinoma, and ovarian cancer.

A method for predicting the therapeutic effectiveness to treat a carcinoma that overexpresses HER-2 with a therapeutic agent, wherein the therapeutic agent is a HER-2 binding ligand, comprising:

(a) providing a tumor tissue sample having tumor cells contained therein;

(b) providing an antibody that binds to a stub region of HER-2, wherein the stub region is a polypeptide sequence, of SEQ ID NO. 1 or a fragment thereof, and (c) determining the percentage of cells that have an exposed extracellular stub region, wherein a high percentage of tumor cells binding to the antibody indicates that the cancer will likely be resistant to the therapeutic agent.

Preferably, the means for determining the percentage of cells having an exposed extracellular stub region utilizes an assay procedure, wherein the assay procedure is selected from the group consisting of Western blotting, immunochemistry, red cell agglutination, ELISA, affinity chromatography, and combinations thereof. Preferably, the carcinoma that overexpresses HER-2 is selected from the group consisting of breast carcinoma, gastric carcinoma, prostate cancer, non-small lung carcinoma, and ovarian cancer. Preferably, the therapeutic agent is a humanized monoclonal antibody that binds to the extracellular domain of HER-2 (Herceptin).

A method for treating HER-2/neu-positive carcinomas, comprising administering an effective amount of a hydroxamate compound. Preferably, the hydroxamate compound is TAPI.

The present invention provides a method for determining node status in breast cancer prognosis, comprising:

(a) providing a suspected tissue sample having cells;

(b) dividing the tissue sample for measuring both p95HER-2 intracellularly and p185HER-2;

(c) lysing the cells to expose intraycellular contents and form a lysate for p95HER-2 assay;

(d) measuring the tissue sample for p185HER-2; and (e) measuring the lysate for the presence of 95HER-2 polypeptide, wherein tissue samples that were both p95HER-2 positive and rich with p185HER-2 predict lymph node or other metastasis.

Preferably, the lysing step is followed by an additional step separating soluble from insoluble material of the lysate to remove dense fibrous material. Preferably, the measuring step utilizes an assay procedure selected from the group consisting of Western blotting, immunochemistry, ELISA, and combinations thereof.

DETAILED DESCRIPTION OF THE INVENTION

The present invention is based upon the initial identification and characterization of a N-terminally truncated HER-2/neu protein (p95HER-2 or simply p95) and a subsequent examination and correlation with ECD shedding and association with breast cancer pathologic factors.

Figure 1:
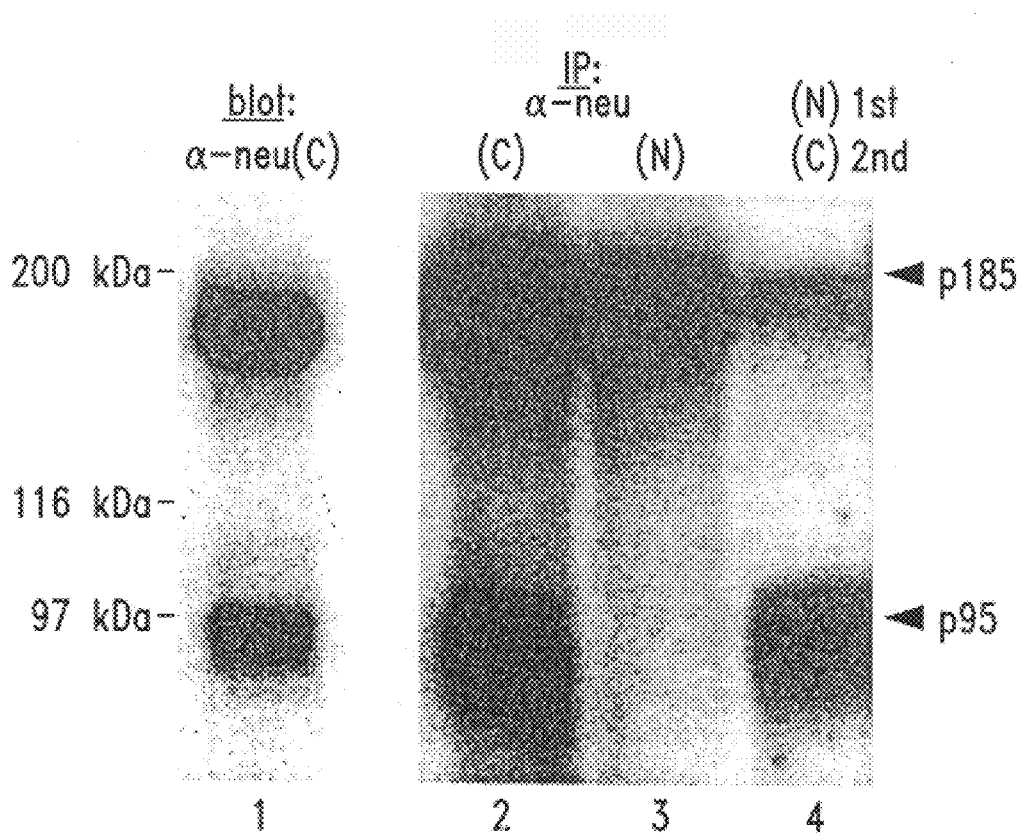
FIG. 1 shows an N-terminally truncated HER-2/neu product having kinase enzymatic activity. About 25 µg of protein from 17-3-1 cells were western blotted with anti-neu (C) diluted 1:10,000 (lane 1). In lanes 2–4, 400 µg protein were immunoprecipitated with anti-neu (C) (lanes 2,4) or with monoclonal antibody against the extracellular domain, anti-neu(N) (lane 3), or depleted of p185HER-2/neu by extracting twice with anti-neu(N) and then immunoprecipitated with anti-neu(C) (lane 4). The immune complexes were phosphorylated with ($^{-32}$P) ATP and analyzed by SDS-PAGE and autoradiography, demonstrating kinase activity.

The present invention identified an N-terminally truncated HER-2/neu product of about 95 kDa, which was detected by Western blotting and by immunoprecipitation with anti-peptide antibodies against the C-terminus, but did not react with monoclonal antibodies against the N-terminus of p185HER-2/neu. P95HER-2 has kinase activity evidenced by its self-phosphorylation when p185HER-2 was cleared from the cell extract prior to immunoprecipitation with anti-neu (C) (FIG. 1). Several controls and extraction procedures were conducted to rule out that p95 was created by an in vitro degradation artifact. Cells extracted with protease inhibitors had only two major cytoplasmic HER-2/neu proteins, p95HER-2 and p185HER-2, with no indication of smaller degradation products. P95HER-2 levels were not affected by procedures that would eliminate the activity of proteases including direct extraction of cells in boiling 10% SDS-containing buffers.

Figure 4:
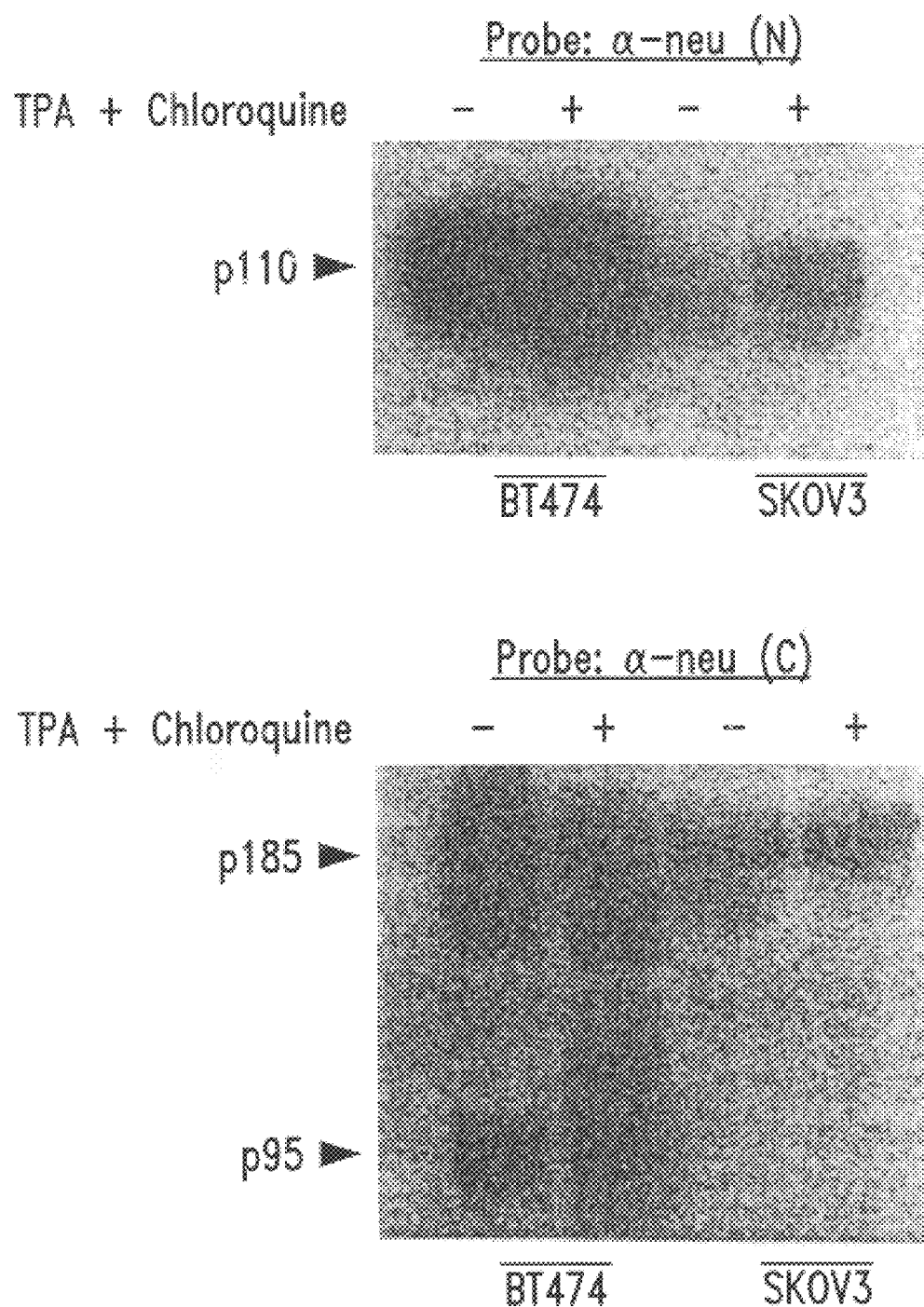
FIG. 4 shows the expression of p95 and ECD in SKOV3 and BT474 cells. Cells were treated for 24 hrs in serum-free medium with control vehicle or with 500 nM of the phorbol ester TPA and 50 μM chloroquine. In the top panel (FIG. 4A), 5 ml of conditioned media was concentrated 100 fold, denatured under nonreducing conditions, and aliquots normalized to cell extract protein were analyzed by western blotting with anti-neu (N) monoclonal antibody at 1 μg/ml. In the lower panel (FIG. 4B), 20 μg of cell proteins were analyzed by Western blotting using anti-neu (C). The data shown in FIG. 4 are representative of three replicate experiments.

One mechanism previously described for generation of N-terminally truncated receptor tyrosine kinases is by proteolytic release of their ECD (Downing et al., *Mol. Cell. Biol.* 9:2890–2896, 1989; Cabrera et al., *J. Cell. Biol.* 132 427–436, 1996; O'Bryan et al., *J. Biol. Chem.*, 270:551–557, 1995; and Vecchi et al., *J. Biol. Chem.* 271:18989–18995, 1996). Production of p95HER-2 in cultured cells occurs by endoproteolytic processing. The presence of p95HER-2 in 17-3-1 cells transfected with HER-2/neu cDNA indicates that p95HER-2 is a proteolytic product rather than the product of an alternative transcript. Furthermore, the levels of p95HER-2 and soluble HER-2 ECD released from cultured cells were correlated. First, both p95HER-2 and ECD levels were low in SKOV3 cells compared to BT474 cells (FIG. 4). Secondly, augmentation of both p95HER-2 and ECD by long term (24 hr) treatment with TPA and chloroquine (FIG. 4) further indicated that the truncated HER-2 products were generated through a common pathway.

Figure 5:
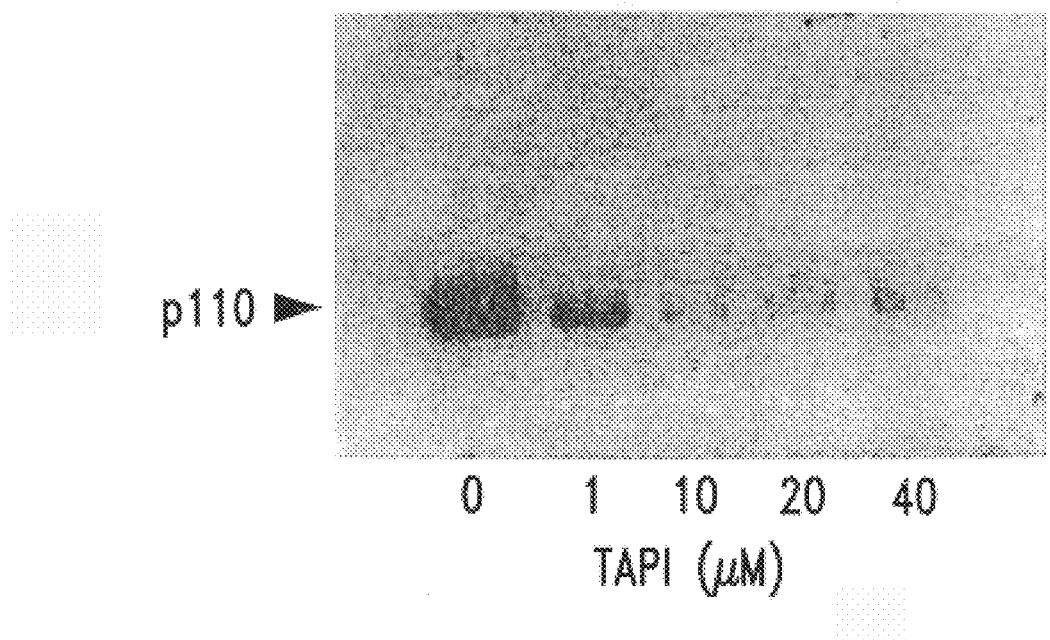
FIG. 5 shows the results of experiments showing that P95HER-2 and ECD are inhibited by the hydroxamic acid, TAPI. BT474 cells in serum-free medium were treated for 24 hrs with the control vehicle or with 1, 10, 20, and 40 μM TAPI (a gift from Immunex, Seattle, Wash.). In the top panel (FIG. 5A), the concentrated, conditioned media, normalized to the amount of cell extract, were analyzed by western blotting with anti-neu (N). Similar results were obtained when 5 μg of protein from the conditioned media from each culture were analyzed. In the lower panel (FIG. 5B), 20 μg of cell proteins were analyzed by Western blotting using anti-neu (C).
Figure 5:
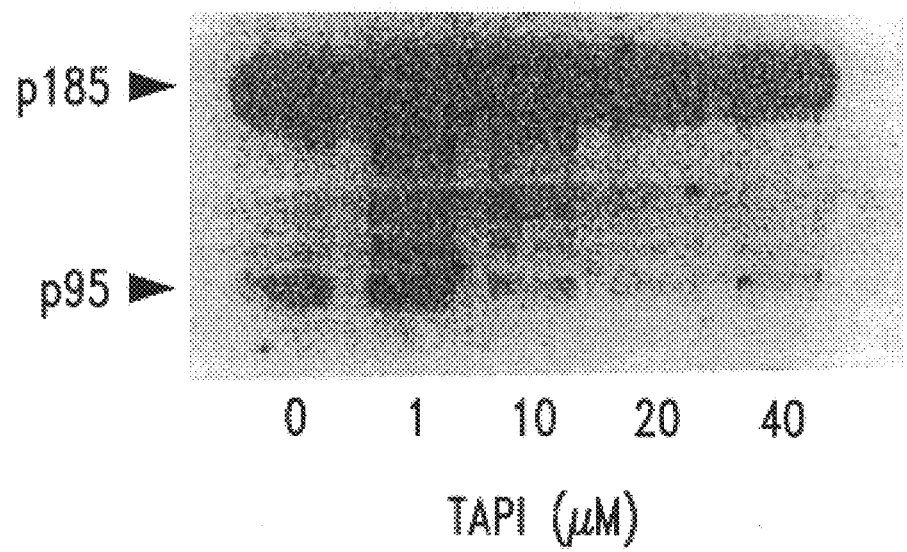

Although the mechanism for this stimulation was not examined directly, long term exposure of cells to TPA has been found to enhance internalization of RTKs (receptor tyrosine kinases) (Seedorf et al. *J. Biol. Chem.* 270:18953–18960, 1995). Moreover, chloroquine, an agent that alters pH in cellular endosomes and lysosomes, inhibited complete proteolytic breakdown or altered RTK trafficking (Marshall, *J. Biol. Chem* 260:4136–4144, 1985). Finally, both p95HER-2 and ECD levels from intact cells were inhibited by the hydroxamate compound, TAPI. Inhibition was maximal at a TAPI concentration of 10 μM or less (FIG. 5). The strong inhibition by TAPI indicates that most of the ECD and p95HER-2 in BT474 cells were generated by a metalloprotease (McGeehan et al., *Nature* 370:561, 1994; and Mohler et al., *Nature* 370:218–220, 1994) and that this class of protease inhibitors is effective in controlling shedding in breast cancer patients. Although p95HER-2 and shedding were modulated under several different conditions, changes in cellular p185HER-2 levels could not be detected. Unlike several transmembrane proteins that only shed when induced by TPA, proteolytic shedding of p185HER-2 occurs continually at a low basal level (Lin and Clinton, *Oncogene* 6: 639–643, 1991; and Zabrecky et al., *J. Biol. Chem.* 266: 1716–1720, 1991) with only about 20% converted into soluble ECD in 2 hrs (Pupa et al., *Oncogene,* 8:2917–2923, 1993).

The truncated cell protein of about 95 kDa described herein was somewhat larger than the expected 75–80 kDa for the cytoplasmic remnant of the ~105–110 kDa ECD. ECD is a glycosylated protein with multiple bands on gel migraton. P95HER-2 or the ECD might migrate anomalously in gels, since the site of cleavage for ECD shedding is not known. The ECD and p95HER-2 are coordinately produced in culture by proteolytic activity that is sensitive to a metalloprotease inhibitor.

Figure 2:
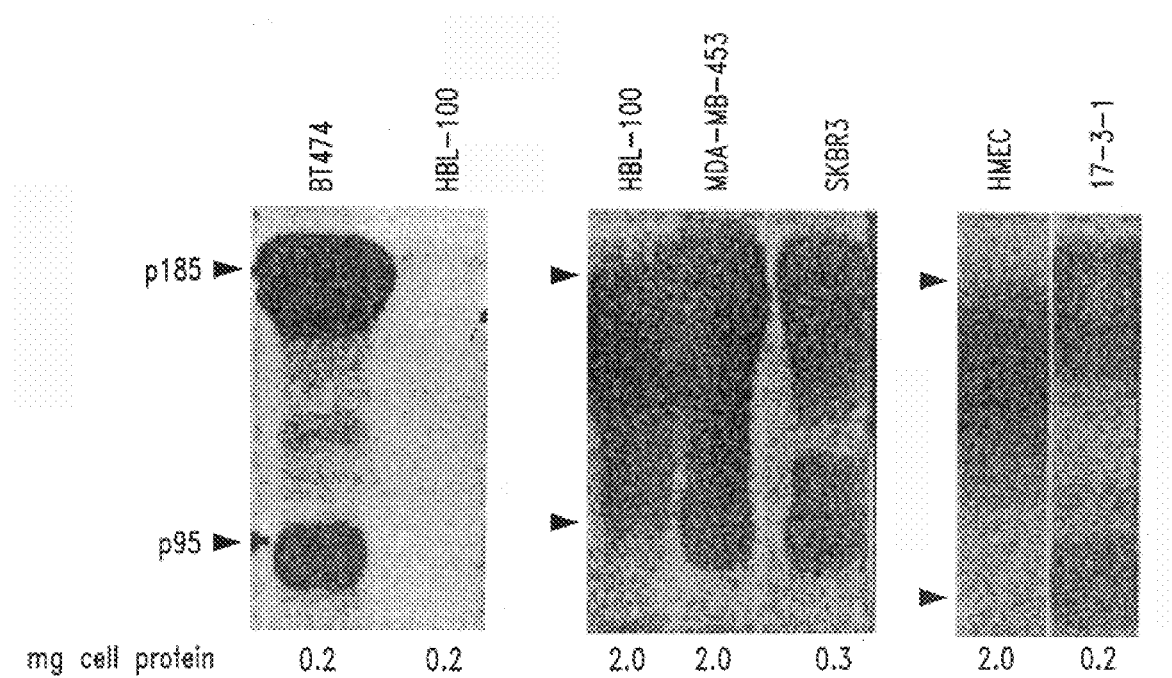
FIG. 2 shows that human breast carcinoma cell lines contain p95HER-2/neu. Indicated amounts of cell lysates from BT474, HBL-100, MDA-MB-453, SKBR3, HMEC, and 17-3-1 cells were immunoprecipitated with anti-neu (C) and phosphorylated following the same procedure described for FIG. 1 above.

A HER-2/neu product of the same size, 95 kDa, in transfected 3T3 cells, cultured breast carcinoma cells, breast cancer tissue, and ovarian cancer tissue indicates that a similar proteolytic processing event occurs in the different cells. However p95HER-2 was not detected in all cells and tumor tissue that contain p185HER-2. Two nontumorigenic breast epithelial cell lines had no detectable p95HER2 (FIG. 2). In addition, the SKOV3 ovarian carcinoma cells, which overexpress p185HER-2, had a disproportionately low amount of p95HER-2 (FIG. 4). These observations indicate that production of p95HER-2 is regulated. The cells with variable levels of truncated HER-2/neu products may differ in the amount of the relevant protease activity or the protein substrate may have an altered conformation affecting sensitivity to proteolytic cleavage.

P95HER-2/neu has kinase enzymatic activity. It is tyrosine phosphorylated and it is truncated from its N-terminus. Oncogenic signaling by HER-2/neu depends upon its level of kinase activity (DiFiore et al., Science 237:178–182, 1987; Hudziak et al., Proc. Natl. Acad. Sci. USA 84: 7159–7163, 1987; and Segatto et al., Mol. Cell. Biol. 8:5570–5574, 1988). Since p95HER-2 was at 100% of p185HER-2 in some breast cancer samples, it may impact the amplitude of the kinase: signal. Moreover, an N-terminally truncated kinase domain, such as p95HER-2, is expected to emit a constitutive signal by analogy to results with engineered deletions of the ECD from the HER-2/neu product (Vecchi et al., J. Cell. Biol. 139:995–1003, 1997; DiFiore et al., Science 237:178–182, 1987; Hudziak et al., Proc. Natl. Acad. Sci. USA 84: 7159–7163, 1987; Segatto et al., Mol. Cell. Biol. 8:5570–5574, 1988; and Bargmann and Weinberg, EMBO J. 7:2043–2052, 1988). Taken together these data provided herein indicate that p95HER-2 will elevate the kinase signal in some patients and is thereby associated with more aggressive tumor growth.

Cancer tissues were analyzed by Western blotting and scored for p95HER-2 and for p185HER-2/neu expression. Breast and ovarian cancer tissues were both found to express p95HER-2 in addition to p185HER-2/neu. Of 161 breast cancer tissues studied, 22.4% expressed p95HER-2, 21.7% overexpressed p185HER-2, and 14.3% were both p95HER-2 positive and overexpressed p185HER-2. A higher proportion of node positive patients (23 of 78) than node negative patients (9 of 63) expressed p95HER-2 in all tumors combined (P=0.032). In the group that overexpressed p185HER-2, those that contained p95HER-2 were associated with node positive patients: (15 of 21) whereas those that were p95 negative were associated with node negative patients (8 of 11) (P=0.017). Neither p95HER-2 nor p185HER-2-rich patients significantly correlated with tumor size or with hormone receptor status in this study. These data indicate that breast cancers, which express the HER-2/neu oncogene, are heterogeneous with respect to HER-2/neu protein products. Moreover, p95HER-2/neu appeared to distinguish tumors that have metastasized to the lymph nodes from those in node negative patients.

In the following examples, 161 breast cancer tissues were homogenized, fractionated and analyzed by Western blotting, a technique that can distinguish p185HER-2 from its truncated cytoplasmic protein, p95HER-2. A study conducted by Tandon et al, (Tandon et al., J. Clin. Oncol. 7: 1120–1128, 1989) also used Western analysis of breast tissue extracts, but Tandon et al. only evaluated the full length product, p185HER-2. The data provided herein are consistent with the results reported in Tandon et al. The data in the examples also found p185HER-2 to be expressed frequently in breast tumors with a subpopulation of 21.7%, compared to Tandon et al's 16% that was scored as highly positive. These results are consistent.

The data in the examples herein show that breast cancers, which express HER-2/neu, are heterogeneous with respect to protein products. The distinct products, p95HER-2 and p185HER-2, were differentially associated with node status. While the group that overexpressed p185HER-2 did not associate with node status (Table 1), those that were p185-rich and contained p95HER-2 were significantly associated with lymph node metastasis (Table 2). This may help explain why several previous studies, which have attempted to show association with lymph node metastasis based on assays of p185HER-2 protein overexpression or HER-2/neu gene amplification, have yielded inconsistent results (see, for example, Singleton and Strickler, Pathol.Annual 27 Pt 1:165–198, 1992). Without being bound by theory, a biological explanation for these data is that loss of the ECD regulatory region from the p95HER-2 kinase, combined with amplified p185HER-2 signal in primary breast tumor cells, promotes their metastasis, such as to the lymph nodes.

P95HER-2 positive or p185HER-2 highly positive samples did not correlate with other prognostic markers in these data, including tumor size or hormone receptor status. While no consistent correlation with tumor size has been detected, other studies have reported association of HER-2/neu overexpression with ER and PR negativity (Singleton and Strickler, Pathol.Annual 27 Pt 1:165–198, 1992; Tandon et al., J. Clin. Oncol. 7: 1120–1128, 1989; and Carlomagno et al., J. Clin. Oncol., 14:2702–2708, 1996). Moreover, in contrast to the data reported herein, the relationship between HER-2 overexpression and hormone receptor status was examined in a subgroup of high-risk patients or in groups that were stratified by levels of hormone receptors (Tandon et al., J. Clin. Oncol. 7: 1120–1128, 1989; and Carlomagno et al.; and J. Clin. Oncol., 14:2702–2708, 1996).

In conclusion, HER-2/neu overexpression in tumor tissue is a strong prognostic marker only in node positive patients (Slamon et al., Science 244: 707–712, 1989; Singleton and Strickler, Pathol.Annual 27 Pt 1:165–198, 1992; Slamon et al., Science 235:177–182, 1987; Press et al., Progress in Clinical & Biological Research 354:209–221, 1990; Hynes et al., Biochem. Biophys. Acta 1198:165–184, 1994; and Tandon et al., J. Clin. Oncol. 7: 1120–1128, 1989). The data presented herein indicate that p95-2 is preferentially found in HER-2/neu positive patients with lymph node involvement. Higher expression of p95HER-2 is a critical factor that helps explain the increased prognostic significance of HER-2/neu in node positive patients.

Both ECD and p95 were at about 20 fold lower levels in SKOV3 ovarian carcinoma cells compared to BT474, breast carcinoma cells. Both were stimulated by treatment of cells with the phorbol ester tumor promoter (TPA) and the lysosomotrophic agent, chloroquine. The hydroxamate inhibitor of metalloproteases, TAPI, suppressed both p95 and ECD (HER-2/neu extracellular domain) in a dose-dependent fashion with maximal inhibition at 10 $\mu$M or less in BT474 cells.

Proteolytic release of the ECD is expected to create an N-terminally truncated, membrane-associated fragment with kinase activity.

P95HER-2

P95HER-2 is the C-terminal polypeptide fragment of p185HER-2, whose complete sequence was first published in Coussens et al., Science 230:11,32–1139, 1985. P185HER-2 is a 1255 amino acid polypeptide ending in Val residue at position 1255. The N-terminus of p95HER-2 begins from about Asp at position 639 to about the Glu residue at position 645. Most likely, the N-terminal residue is Pro from position 643.

Hydroxamate Compounds

The present invention further provides a method for treating carcinomas that overexpress HER-2, comprising administering a hydroximate compound, wherein the hydroximate compound is described in formula 1:

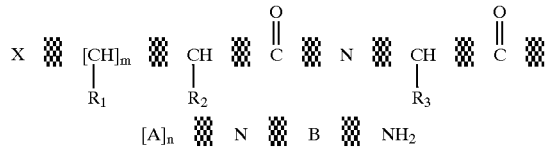

wherein: X is hydroxamic acid, thiol, phosphoryl or carboxyl; m is 0, 1 or 2; $R_1$, $R_2$, and $R_3$ is independently hydrogen, alkylene(cycloalkyl), $OR_4$, $SR_4$, $N(R_4)(R_5)$, halogen, a substituted or unsubstituted $C_1$ to $C_6$, alkyl, $C_1$ to $C_6$ alkylenearyl, aryl, a protected or unprotected side chain of a naturally occurring α-amino acid; or the group $R_6R_7$, wherein $R_6$ is substituted or unsubstituted $C_1$ to $C_8$ alkyl and $R_7$, is $OR_4$, $SR_4$, $N(R_4)(R_5)$ or halogen, wherein $R_4$ and $R_5$ are independently hydrogen or substituted or unsubstituted $C_1$ to $C_8$ alkyl; wherein n is 0, 1 or 2; with a first proviso that when n is 1, A is a protected or an unprotected α-amino acid radical; and with a second proviso that when n is 2, A is the same or different protected or unprotected α-amino acid radical; and wherein B is an unsubstituted or substituted $C_2$ to $C_8$ alkylene. Methods for synthesizing compounds of formula 1 are disclosed in U.S. Pat. No. 5,629,285, the disclosure of which is incorporated by reference herein. Pharmaceutical formulations are compositions are also disclosed in U.S. Pat. No. 5,629,285.

EXAMPLE 1

This example illustrates the identification of N-terminally truncated HER-2/neu protein with kinase activity. 3T3 cells were transfected with HER-2/neu cDNA (17-3-1 cells) (Applied BioTechnololgy, Inc. Cambridge, Mass.) and release soluble ECD by proteolytic processing of p185HER-2/neu (Zabrecky et al., *J. Biol. Chem.* 266: 1716–1720, 1991). To detect truncated cytoplasmic products: 17-3-1 extracts were resolved in gels and immunoblotted with antibodies against the C-terminus of the HER-2/neu product (anti-neu (C)). 17-3-1 Cells, were cultured in Dulbecco's modified Eagles medium (DMEM) supplemented with 5% fetal bovine serum containing 0.4 mg/ml geneticin (G418 GIBCO-BRL). Briefly, anti-neu (C) has been described (Lin et al., *Mol. Cell. Endocrin.* 69: 111–119, 1990). Monoclonal antibody against the extracellular domain of HER-2/neu was prepared as described (McKenzie et al., *Oncogene*, 4:543–548, 1989) and was provided by Applied BioTechnology Inc. Briefly, freshly prepared cell lysates in TEDG buffer (50 mM Tris, 1.5 mM EDTA, 0.5 mM dithiothreitol, 10% glycerol pH 7.5 with 1% aprotinin, 2 mM PMSF, and 2 mM vanadate) containing 1% Nonidet P-40 were immunoprecipitated by incubation with antibody for 2 hrs with continuous shaking at 4° C. as described (Lin et al., *Mol. Cell. Endocrin.* 69: 111–119, 1990). The immune complexes, bound to Protein G Sepharose (Pharmacia), were washed twice with TEDG buffer and incubated 10 min on ice in a kinase reaction mixture containing 20 mM HEPES pH 8.0, 2 mM dithiothreitol, 25 µM vanadate, 0.5% Nonidet P-40, 10 mM $MnCl_2$, 1 µM ATP, and 15 µCi ($\gamma$-$^{32}$P)ATP (New England Nuclear). The immune complexes were washed 3 times with buffer and the proteins were released by boiling for 2 min in SDS-PAGE sample buffer.

Two major protein products were detected in cell extracts; the full length p185 HER-2/neu and a truncated protein of about 95 kDa (FIG. 1, lane 1). The extracts were immunoprecipitated and the 95 kDa protein, as well as p185HER-2/neu, were phosphorylated in the immune complex with ($\gamma$-$^{32}$P)ATP (FIG. 1, lane 2). A monoclonal antibody specific for the N-terminal region of p185HER-2/neu (anti-neu (N)) did not immunoprecipitate p95HER-2, indicating that the N-terminal region was missing (FIG. 1, lane 3). Therefore, p95HER-2 is a fragment of p185HER-2 and is no an N-terminal fragment.

EXAMPLE 2

This example illustrates that p95HER-2 has self-phosphorylating activity and was not the substrate of the full length receptor tyrosine kinase. P185HER-2 was first removed from the cell lysate with anti-neu (N), and then p95HER-2 was immunoprecipitated with anti-neu (C) as described in example 1. P95HER-2 was phosphorylated when p185HER-2 levels were greatly depleted (FIG. 1 lane 4). These data indicate that p95HER-2 has kinase enzymatic activity.

Moreover, p95HER-2 kinase activity is in human breast carcinoma cells but not in nontumorigenic breast epithelial-cells. The human breast carcinoma cell line, BT474, known to release soluble ECD (Lin and Clinton, *Oncogene* 6: 639–643, 1991) also contains two autophosphorylated HER-2/neu products, p185HER-2 and p95HER-2. The human breast carcinoma cell line BT474 was cultured in RPMI medium supplemented with 10% FBS and 10 µg/ml insulin. Both were found at elevated levels compared to the nontumorigenic breast epithelial cell line HBL-100 (FIG. 2). It was possible that p95 could not be detected in the small amount of HBL-100 cells, since they express low levels of p185HER-2 (Kraus et al., *EMBO J.* 6:605–610, 1987). To compensate for different levels of HER-2/neu expression (Kraus et al., *EMBO J.* 6:605–610, 1987), the amounts of extract from HBL-100, human mammary epithelial cells, (HMEC), and three breast carcinoma cell lines were adjusted and proteins were phosphorylated with ($\gamma$-$^{32}$ P) ATP. P95HER-2 was detected in the low (MDA-MB-453) and high (BT474 and SKBR3) HER-2/neu expressing breast carcinoma cells, but not in the HBL-100 nor HMEC cells, despite a robust signal from the HER-2/neu receptor which migrated as a slightly smaller protein in the breast epithelial cells (FIG. 2).

EXAMPLE 3

This example illustrates that p95HER-2 is a tyrosine phosphorylated polypeptide with kinase enzymatic activity and is located in the membrane fraction from BT474 cells. Tyrosine phosphorylation of tyrosine kinase receptors generally indicates their activation in signaling (Hynes et al., *Biochem. Biophys. Acta* 1198:165–184, 1994; and Dougall et al., *Oncogene* 9: 2109–2123, 1994). The tyrosine phosphorylation of p95HER-2, and its subcellular location were examined by fractionation of BT474 cell extracts into a soluble fraction and a particulate fraction. Each fraction was immunoprecipitated with anti-neu (C) and then subjected to Western blot analysis using monoclonal antibodies against phosphotyrosine. Briefly, following SDS-PAGE, cell lysates or proteins from concentrated, conditioned medium were electroblotted onto nitrocellulose (Trans-Blot, Bio-Rad) using a semi-dry transfer unit (Bio-Rad) at 15 volts for 20 min per mini gel of 0.75 mm thickness (Mini-PROTEAN II electrophoresis cell, BioRad) equilibrated with 25 mM Tris pH 8.3, 192 mM glycine, 50 mM NaCl, 20% methanol. Binding sites were blocked by incubating the membrane with 5% nonfat dry milk. After incubation with the primary antibody, the blot was washed twice for 15 min and 4 times for 5 min with Tris-buffered saline (TBS) containing 0.05% Tween and then incubated for 40 min with goat anti-rabbit or goat anti-mouse antibody conjugated to horseradish peroxidase (HRP) (Bio-Rad) diluted in TBS-Tween. After incubation with secondary antibody, the blot was washed as described above with TBS-Tween and developed with chemiluminescent reagent (Pierce).

Figure 3:
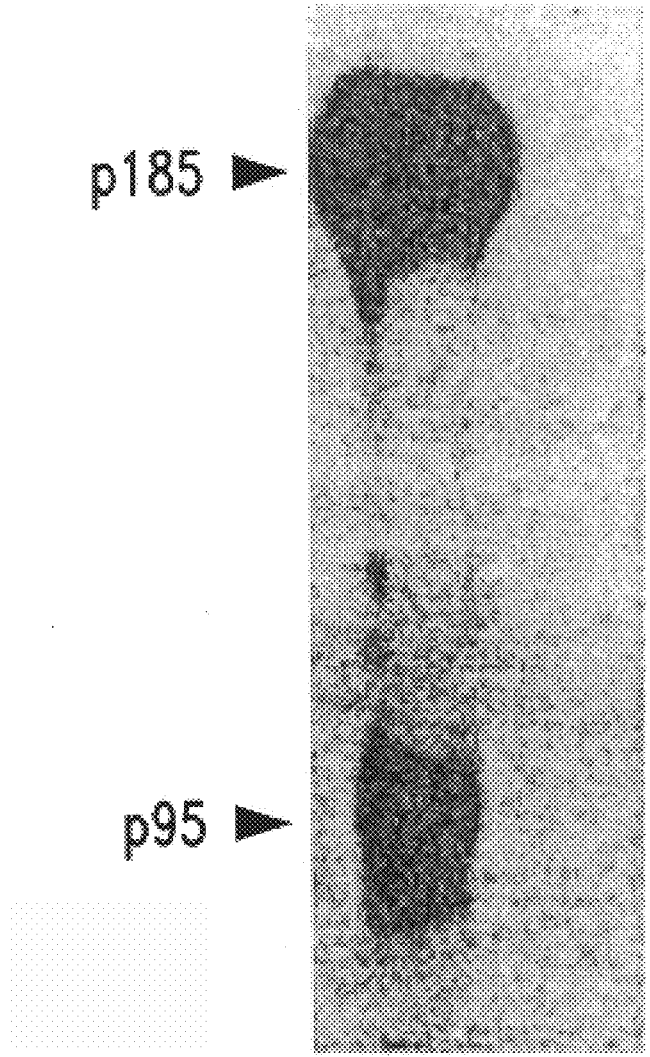
FIG. 3 provides the results of an experiment wherein tyrosine phosphorylation of p95 localized in a particulate fraction of BT474 breast carcinoma cells. Particulate (P) and soluble (S) fractions were prepared by incubation of $10^7$ cells in ice for 10 min in 3 ml of homogenization buffer (10 mM Tris pH7.4, 10 mM NaCl, 2 mM $MgCl_2$ with 2 mM vanadate and protease inhibitors), followed by dounce homogenization, and then centrifugation at 100,000×g for 1 hr. The pellet was resuspended in 3 ml of homogenization buffer. About 200 μg of protein from the particulate fraction and an equal volume of the soluble fraction were immunoprecipitated with anti-neu (C) and analyzed as a Western blot with monoclonal anti-phosphotyrosine antibody (Sigma). These data show that p95HER-2 is located at the plasma membrane (with p185HER-2) and that p95HER-2 is phosphorylated in vivo, which is an indication of signaling activity.

FIG. 3 illustrates that a tyrosine phosphorylated p95HER-2 fractionated with p185HER-2 in the particulate fraction. The particulate fraction contains the plasma membranes. P95HER-2 was further shown to be tyrosine phosphorylated by first immunoprecipitating with anti-phosphotyrosine antibodies and then probing the Western blot with anti-neu (C) (data not illustrated).

EXAMPLE 4

This example illustrates that p95HER-2 polypeptide intracellular levels corresponded to levels of soluble ECD released from different cells. To examine the relationship of p95HER-2 to soluble ECD, their levels were compared in different cells under varied conditions. The basal levels of ECD and cellular p95HER-2/neu were first examined in two cell lines that overexpress HER-2/neu, BT474 and the ovarian carcinoma cell line SKOV-3. Both cell lines were reported to produce low levels of ECD (Pupa et al., *Oncogene*, 8:2917–2923, 1993).

The amount of p95HER-2, relative to p185HER-2 and to cell protein, was greatly elevated in BT474 cells. Correspondingly, the ECD in the extracellular medium from BT474 cells, detected with anti-neu (N), was enhanced by greater than 10 fold compared to the SKOV3 cells (FIG. 4).

Shedding of several membrane proteins is rapidly and transiently induced by phorbol ester tumor promoters (Ehlers and Riordan, *Biochem. J.* 321:265–279, 1997). While short term treatment with tumor promoters does not induce HER-2 shedding (Vecchi et al., *J. Biol. Chem.* 271:18989–18995, 1996), chronic administration of the phorbol ester TPA synergized with chloroquine to stimulate release of soluble HER-2.

To determine whether p95HER-2 and ECD were coordinately regulated, TPA (500 nM) and chloroquine (50 $\mu$M) or the control vehicle were added to the culture media of BT474 and SKOV3 cells. SKOV3 cells were grown in DMEM supplemented with 10% FBS and the antibiotic gentamicin at 0.05%. At 24 hrs, the ECD levels in the extracellular media and p95HER-2 levels in the cell extract were analyzed. Soluble ECD was elevated several fold in the conditioned medium from stimulated BT474 cells and SKOV3 cells, while p95HER-2 was upregulated about three-fold in BT474 cells (FIG. 4). Overexposure of the immunoblot revealed that p95HER-2 in SKOV3 cell extracts was also stimulated about three-fold by TPA and chloroquine (data not illustrated in figures).

EXAMPLE 5

This example, illustrates that a metalloprotease inhibitor depressed levels of p95HER-2 and ECD from BT474 cells. Shedding of diverse transmembrane proteins is inhibited by hydroxamic acid-based compounds, which are potent metalloproteinase inhibitors (McGeehan et al., *Nature* 370:561, 1994; Mohler et al., *Nature* 370:218–220, 1994; and Arribas et al., *J. Biol. Chem.* 271:11376–11382, 1996). Therefore, effects of different concentrations of the hydroxamic acid, TAPI (Mohler et al., *Nature* 370:218–220, 1994) was tested on shedding of HER-2/neu ECD and on cell levels of p95. TAPI (0 to 40 $\mu$M) was added to cultured BT474 cells for 24 hrs, the ECD in concentrated conditioned media was analyzed by immunoblotting with anti-neu (N), and p95HER-2 and p185HER-2 polypeptides were examined in cell extracts using an anti-neu (C) monoclonal antibody. The results in FIG. 5 show that production of ECD was partially inhibited at a 1 $\mu$M TAPI concentration and maximally inhibited at a 10 $\mu$M TAPI concentration. A residual amount of about 10% of the ECD resisted inhibition by even 40 $\mu$M TAPI. The level of truncated p95HER-2 in the cytoplasm was also inhibited by TAPI, with little or no effect at a 1 $\mu$M concentration and maximal inhibition at a 10 $\mu$M concentration (FIG. 5). These data were reproducible in another cell line.

In three separate experiments, 1 $\mu$M TAPI inhibited ECD and p95HER-2 levels by 50% or less, and in all cases, maximum inhibition was achieved by a 10 $\mu$M concentration of TAPI. No change in p185HER-2/neu levels could be detected in cells treated with TAPI or when shedding was stimulated by TPA and chloroquine (FIG. 4). Without being bound by theory, but these results are because proteolytic processing of p185HER-2 is constitutive and limited with about 20% converted into soluble HER-2/neu in 2 hrs (Pupa et al., *Oncogene*, 8:2917–2923, 1993). TAPI also increased p95HER-2 in a cell line, however different mechanisms of action may apply.

EXAMPLE 6

This example illustrates the detection of p185HER-2 and p95HER-2 in breast cancer tissue. Tumor tissues were homogenized, fractionated, and examined for HER-2/neu proteins by Western analysis. Briefly, about 0.1 gm of tumor tissue, which had been fresh-frozen and stored at −70° C., was minced on dry ice and suspended in TEDG buffer. Tissues were homogenized using a Brinkman polytron for 5–10 second bursts repeated 2–3 times with a chilled probe. Homogenates were centrifuged at 1500×g for 10 min at 4° C. The lipid layer was removed with a wooden stick and the supernatant was centrifuged for 20 min at 40,000×g at 4° C. The lipid layer was collected with a wooden stick, the supernatant decanted, and the pellet containing the membranes was solubilized in TEDG buffer containing 0.1% SDS for 20 min with intermittent vortexing and clarified by centrifugation at 15,000×g for 15 min. The protein concentration in the supernatant was determined by the Bio-Rad protein assay reagent and aliquots were frozen at −80° C.

P95HER-2 and p185HER-2 in breast cancer tissue were analyzed according to the following method. About twenty $\mu$g of protein from the membrane fraction prepared from each tumor sample was resolved under denaturing and reducing conditions by SDS-PAGE in 10% gels. Each gel also contained 3 $\mu$g of protein from extracts of 17-3-1 cells to mark the migration of p185 and p95 and to provide a standard for the entire study. Proteins were electrotransferred onto membranes as described above, which were incubated with anti-neu (C) diluted 1:10,000 in TBS-Tween at 4° C. overnight with shaking and then incubated with a 1:10,000 dilution of goat anti-rabbit HRP conjugated antibody (Bio-Rad) for 40 min at room temperature. To develop the blot, the membranes were incubated with chemiluminescent reagent (Pierce) for 5 min and then exposed to Kodak X-OMAT AR film for 1, 5, 20, and 120 min. To define the samples that overexpressed p185HER-2/neu, specimens with HER-2 immunoassay values that were considered HER-2/neu-rich (400 units or greater) compared to samples with low HER-2/neu levels (less than 400 units) were characterized for their p185HER-2 signal relative to the control 17-3-1 cells by western analysis. Those samples with a p185HER-2 signal that could be detected by 1 min exposure of the membrane to film and that was equal to or greater than the p185HER-2 levels found in 3 μg of 17-3-1 cells, as revealed by laser densitometric analysis of the film, were scored as highly positive.

A HER-2/neu tissue extract ELISA assay was run on the extracted samples. Briefly, aliquots of membrane-rich fractions prepared from breast cancer tissue as described above were assayed using the Triton Diagnostics c-erbB-2 Tissue Extract EIA kit (Ciba Corning) according to manufacturer's instructions. This assay employs two monoclonal antibodies against the HER-2/neu ECD. The HER-2/neu units/mg protein in the specimens was calculated from a calibration curve generated by plotting the HER-2/neu concentration of the calibration standards versus the absorbance obtained from the immunoassay.

Clinical information on tissue from each patient included information for age, nodal status, size of the primary tumor, age of the patient, stage of disease at diagnosis, estrogen receptor (ER) levels and progesterone receptor (PR) receptor levels. Specimens were considered ER positive and PR positive if they contained at least 10 fmol specific binding sites per mg of cytosolic proteins. The stage of the specimens included 1 at stage 0, 32 at stage I, 56 stage II, 45 stage III and 13 stage IV. Fourteen specimens were of unknown stage. The average age of the patients was 60. The 8 ovarian cancer tissues included 3 that were grade III and 5 that were grade IV.

Using this method, 21.7% of the samples overexpressed p185HER-2. This proportion is comparable to the 15–30% of breast cancers found to overexpress HER-2/neu in numerous clinical studies. In the samples that had detectable p95HER-2, its level ranged from 10% to 100% of p185. In this study, specimens were scored as positive if p95HER-2 was detected at a 10% or greater proportion of p185HER-2 by 2 hrs of exposure of the membrane to film. Because of the high titer of the primary antibody, anti-neu (C), there were rarely any background bands, even when the immunoblots were exposed to film for 2 hrs.

Figure 6:
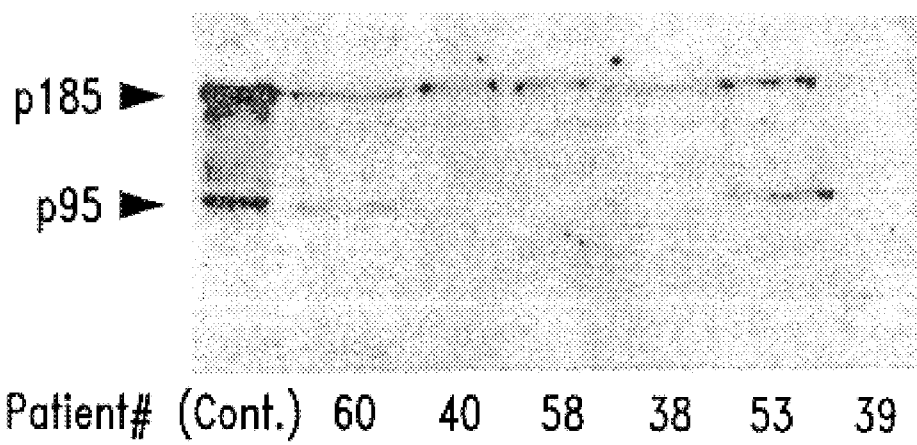
FIG. 6 shows a Western blotting analysis of 12 breast cancer tissues. Human intraductal breast cancer tissues were fractionated and 20 μg of protein from 12 patients were subjected to western blotting with anti-neu (C) as described in FIG. 1, lane 1. The control lane contained 3 μg protein from transfected 3T3 cells and 17-3-1 cells. The position of p185, the top band, and p95HER-2 the lower band, are marked in the control 17-3-1 sample in the lower panel (FIG. 6B). The top panel is a photograph of the film that was exposed to the membrane for 20 min and the bottom panel was exposed for 5 min. HER-2/neu immunoassay values were: <100 Units for #60,39,69; 389 U for #40; 258 U for #58; 302 U for #38; 200 U for #53; 2000 U for #04; 10,000 U for #22; 1000 U for #57; 550 U for #17; 674 U for #75.
Figure 6:
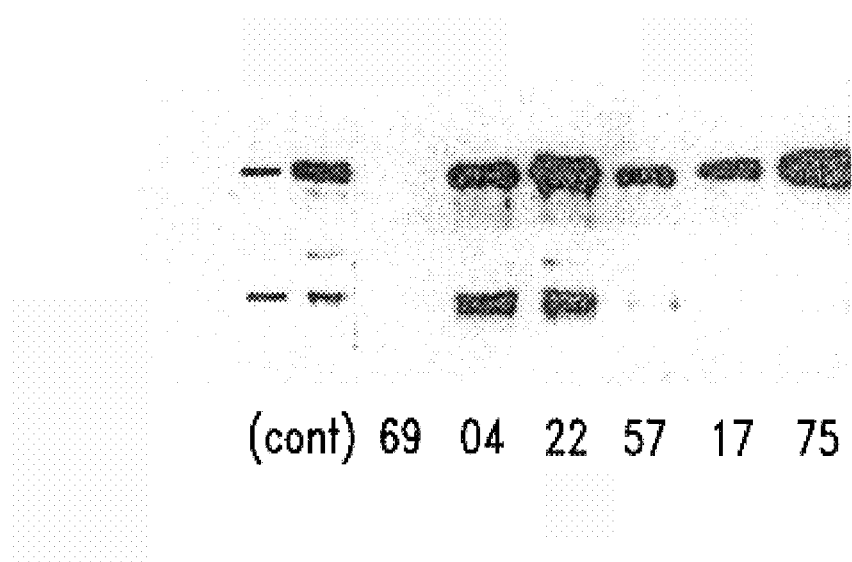

The membrane-enriched but not the soluble fraction (data not shown) from some tumor tissues contained the full-length product, p185HER-2, and the truncated p95HER-2/neu protein that comigrated with HER-2/neu proteins from the control 17-3-1 cells (FIG. 6). In addition, p95HER-2, along with p185HER-2, was detected in 2 of 8 ovarian cancer tissues (raw data not illustrated). Initial analyses of several breast cancer tissues revealed distinct expression patterns of p95HER-2 and p185HER-2. One group had no detectable p185HER-2 or p95HER-2 (see #'s 39 and 69 in FIG. 6). A second category of tumor specimens expressed both p185HER-2 and p95HER-2 polypeptides (#'s 60, 53, 04, and 22). An additional group contained p185HER-2 with relatively little or no p95HER-2 polypeptide expression (#'s 40, 58, 38, 57, 17, and 75). As observed in previous studies by others, some samples were p185HER-2-rich (#'s 04, 22, 57, 17, and 75). The samples that were characterized as highly positive for p185HER-2 were initially identified by immunoassay values of greater than 400 units. The results of the Western analysis indicated that the tumors were heterogeneous with respect to HER-2/neu protein products and that they can be subdivided based on the presence or absence of p95HER-2.

Western analysis of 161 breast cancer samples revealed that 22.4% were p95HER-2 positive. The p185HER-2 positive samples were further subdivided into "highly positive" or HER-2-rich specimens based on comparisons with HER-2/neu overexpressing samples identified by immunoassay and comparisons with the control 17-3-1 extract. The "highly positive" p185HER-2 tumor samples represented 21.7% of the total. All of the tumor samples that expressed p95HER-2 were also positive for p185HER-2, although 65% of p185 positive tumor samples did not contain detectable levels of p95HER-2 polypeptide. Of the p95HER-2 positive tumor samples, 63.9% were also highly positive for p185HER-2 and 36% had low p185HER-2 levels. Therefore, intracellular p95HER-2 polypeptide detection appears to be a reliable prognosticator indicator.

EXAMPLE 8

This example illustrates a relationship as between p95HER-2 positive tumor samples, p185HER-2 highly positive tumor samples, and other prognostic factors of breast or ovarian cancer. Of 78 node-positive breast cancer patients, a higher proportion expressed p95HER-2 polypeptide in intracelluar tumor samples, than for the node negative patients (P=0.032). Moreover, p185HER-2 rich samples had no significant association with node status (Table 1). Neither p95HER-2 positive nor p185HER-2 rich samples correlated significantly with other factors known to predict poor prognosis (McGuire et al., *N. Engl. J. Med.* 326:1756–1761, 1992) including estrogen receptor and progesterone receptor negativity or tumor size of 3 cm or greater Table 1).

TABLE 1

Relationship between p95 positive, p185 highly positive, and other prognostic factors[a]

| Factor | % p95 Positive | P value | % p185 High Positive | P value |
|---|---|---|---|---|
| Nodes |  | .032 |  | NS[b] |
| Pos (78) | 29.5 |  | 24.4 |  |
| Neg (63) | 14.3 |  | 22.2 |  |
| Tumor Size |  | NS |  | NS |
| ≧3 cm (54) | 27.8 |  | 22.2 |  |
| <3 cm (79) | 17.7 |  | 21.5 |  |
| ER |  | NS |  | NS |
| Neg (37) | 32.0 |  | 29.7 |  |
| Pos (117) | 19.7 |  | 17.9 |  |
| PR |  | NS |  | NS |
| Neg (59) | 23.7 |  | 20.3 |  |
| Pos (95) | 22.1 |  | 23.2 |  |

[a]161 samples were examined by western analysis. Not all samples had information for the factors examined.
[b]NS = not significant.

EXAMPLE 9

This example illustrates an influence of p95HER-2 in the p185HER-2 highly positive group. This experiment began by asking the question why a similar percentage of node positive and node negative patients were p185HER-2-rich (24.4% versus 22.2%, Table 1), while p95HER-2 was associated with node positive patients, since 65.7% of the p185HER-2-rich samples contained p95HER-2. The experiment examined whether the presence or absence of p95HER-2 in the specimens that overexpressed p185HER-2/neu affected the relationship with lymph node status (Table 2). The p185HER-2 highly positive samples that contained p95HER-2 (n=21) had a significantly higher association with metastasis to the lymph nodes, while the p185HER-2 highly positive samples that were negative for p95HER-2 (n=11) were associated with lymph node negative patients (P=0.017).

TABLE 2

Relationship between p185 highly positive samples that are p95 negative versus p95 positive with node status.

| | p185 highly positive[a] | |
|---|---|---|
| | p95 positive n = 21 | p95 negative n = 11 |
| node positive | 71.4%[b] | 27.3% |
| node negative | 28.6% | 72.7% |

[a] The p185 highly positive group (n = 32) was divided into those that contained p95 (n = 21) and those that were p95 negative (n = 11).
[b] The samples that contained p95 had a significantly higher association with node positive patients (15 of 21), and those that were p95 negative correlated with node negative patients (8 of 11) (P = .017).

I claim:

1. A method for diagnostic and prognostic screening of a metastatic stage carcinoma that over-expresses p185HER-2, comprising:
   (a) providing a suspected tissue sample having cells;
   (b) lysing the cells to expose intracellular contents and form a lysate;
   (c) providing an assay useful for measuring at least one of p95HER-2 or tyrosine-phosphorylated p95HER-2; and
   (d) measuring, at least in part by using the assay; the lysate for the presence or amount of p95HER-2 polypeptide, whereby the presence or increased amount of p95HER-2 relative to that of control cells is a diagnostic or prognostic indicator of metastatic stage carcinoma, and wherein the carcinoma that over-expresses p185HER-2 is selected from the group consisting of breast carcinomas and ovarian carcinomas.

2. The method of claim 1 wherein the lysing step is followed by an additional step separating soluble from insoluble material of the lysate to remove dense fibrous material.

3. The method of claim 1 wherein the assay step comprises an assay procedure selected from the group consisting of Western blotting, immunochemistry, ELISA, p95HER-2 auto-phosphorylation assays, p95HER-2 kinase assays, and combinations thereof.

4. A method for diagnostic and prognostic screening of a metastatic stage carcinoma that over-expresses p185HER-2, comprising:
   (a) providing a suspected tissue sample having cells;
   (b) providing an antibody that binds to an exposed extracellular stub region of p95HER-2, wherein the extracellular stub region is exposed upon shedding of p105HER-2 and comprises a polypeptide sequence of SEQ ID NO:1; and
   (c) determining, based at least in part on said antibody binding, the presence or amount of p95HER-2 relative to that of control cells, wherein the presence or increased amount of p95HER-2 relative to that of control cells is indicative of metastatic stage carcinoma, and wherein the carcinoma that over-expresses p185HER-2 is selected from the group consisting of breast carcinomas and ovarian carcinomas.

5. The method of claim 4 wherein determining, based at least in part on said antibody binding, the presence or increased amount of p95HER-2 relative to that of control cells comprises an assay procedure selected from the group consisting of Western blotting, immunochemistry, red cell agglutination, ELISA, affinity chromatography, and combinations thereof.

6. A method for diagnostic and prognostic screening of a metastatic stage carcinoma characterized by over-expression of p185HER-2 and elevated serum levels of p105HER-2 extracellular domain (ECD), comprising:
   (a) providing a suspected tissue sample having cells;
   (b) lysing the cells to expose intracellular contents and form a lysate;

(c) providing an assay useful for measuring at least one of p95HER-2 or tyrosine-phosphorylated p95HER-2; and (d) measuring, at least in part by using the assay, the lysate for the presence or amount of p95HER-2 polypeptide, whereby the presence or increased amount of p95HER-2 relative to that of control cells is a diagnostic or prognostic indicator of metastatic stage carcinoma, and wherein the carcinoma that over-expresses p185HER-2 is selected from the group consisting of breast, ovarian, and prostate carcinomas.

7. The method of claim 6 wherein the lysing step is followed by an additional step separating soluble from insoluble material of the lysate to remove dense fibrous material.

8. The method of claim 6 wherein the assay step comprises an assay procedure selected from the group consisting of Western blotting, immunochemistry, ELISA, p95HER-2 auto-phosphorylation assay, p95HER-2 kinase assay, and combinations thereof.

9. A method for diagnostic and prognostic screening of a metastatic stage carcinoma characterized by over-expression of p185HER-2 and elevated serum levels of p105HER-2 extracellular domain (ECD), comprising:

(a) providing a suspected tissue sample having cells;

(b) providing an antibody that binds to an exposed extracellular stub region of p95HER-2, wherein the extracellular stub region is exposed upon shedding of p105HER-2 and comprises a polypeptide sequence of SEQ ID NO:1; and (c) determining, based at least in part on said antibody bindings, the presence or increased amount of p95HER-2 relative to that of control cells, wherein the presence or increased amount of p95HER-2 relative to that of control cells is indicative of metastatic stage carcinoma, and wherein the carcinoma that over-expresses p185HER-2 is selected from the group consisting of breast, ovarian and prostate carcinomas.

10. The method of claim 9 wherein determining, based at least in part on said antibody binding, the presence or increased amount of p95HER-2 relative to that of control cells comprises an assay procedure selected from the group consisting of Western blotting, immunochemistry, red cell agglutination, ELISA, affinity chromatography, and combinations thereof.

11. The method of claim 1, wherein the assay useful for measuring at least one of p95HER-2 or tyrosine-phosphorylated p95HER-2 comprises using an antibody reagent comprising a monoclonal antibody or an epitope-binding fragment thereof.

12. The method of claim 11, wherein the antibody reagent comprises a p95HER-2-specific monoclonal antibody or an epitope-binding fragment thereof, or an anti-phosphotyrosine antibody.

13. The method of claim 6, wherein the assay useful for measuring at least one of p95HER-2 or tyrosine-phosphorylated p95HER-2 comprises using an antibody reagent comprising a monoclonal antibody or an epitope-binding fragment thereof.

14. The method of claim 13, wherein the antibody reagent comprises a p95HER-2-specific monoclonal antibody or an epitope-binding fragment thereof, or an anti-phosphotyrosine antibody.

15. The method of claim 4, wherein the antibody is a monoclonal antibody or an epitope-binding fragment thereof.

16. The method of claim 9, wherein the antibody is a monoclonal antibody or an epitope-binding fragment thereof.

* * * * *

UNITED STATES PATENT AND TRADEMARK OFFICE
CERTIFICATE OF CORRECTION

PATENT NO.    : 6,541,214 B1
DATED         : April 1, 2003
INVENTOR(S)   : Gail M. Clinton It is certified that error appears in the above-identified patent and that said Letters Patent is hereby corrected as shown below:

<u>Title page,</u>
Item [73], after "Oregon", delete "Heath" and insert therefor -- Health --

Signed and Sealed this

Twenty-ninth Day of July, 2003

JAMES E. ROGAN
*Director of the United States Patent and Trademark Office*

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 11
      (B) TYPE: amino acid
      (C) STRANDEDNESS: single
      (D) TOPOLOGY: linear (ii) MOLECULE TYPE: protein (iii) HYPOTHETICAL: no (iv) ANTI-SENSE: no (v) FRAGMENT TYPE: HER-2 stub region (n-terminal fragment)

(vi) ORIGINAL SOURCE:
      (A) ORGANISM: human (xi) SEQUENCE DESCRIPTION: SEQ ID NO:1:

Pro Ala Glu Gln Arg Ala Ser Pro Leu Thr Ser
              5                 10